United States Patent [19]

Richardson

[11] Patent Number: 4,582,830
[45] Date of Patent: Apr. 15, 1986

[54] PHARMACEUTICAL COMPOSITIONS

[75] Inventor: Betty L. Richardson, Harrow, England

[73] Assignee: Glaxo Group Limited, London, England

[21] Appl. No.: 530,655

[22] Filed: Sep. 9, 1983

[30] Foreign Application Priority Data

Sep. 10, 1982 [GB] United Kingdom ................ 8225853

[51] Int. Cl.$^4$ .......................................... A61K 31/545
[52] U.S. Cl. .................................................. 514/203
[58] Field of Search ......................... 424/246; 514/203

[56] References Cited

U.S. PATENT DOCUMENTS

| | | | |
|---|---|---|---|
| 4,128,715 | 12/1978 | Sharp .................................... | 424/246 |
| 4,160,829 | 7/1979 | Heijboer et al. .................... | 424/246 |
| 4,258,041 | 3/1981 | O'Callaghan et al. ............. | 424/246 |
| 4,329,453 | 5/1982 | Brodie et al. ....................... | 424/246 |

FOREIGN PATENT DOCUMENTS 1380741  1/1975  United Kingdom .

OTHER PUBLICATIONS

Whitter, T. D., Symposium on drug stability, 19th International Congress of Pharmaceutical Sciences, 1959, (Abstract).
Freudenstein, H., J. Biol. Stand., 1978, 6 (3), 243-53, (Abstract).
Wisniewski, W., Math Naturwiss Reihe, 1967, 16 (2), 243-45, (Abstract).
Rybachuk, D. V. et al., Khim Farm Zh, 1979, 13 (1), 85-86, (Abstract).
Rybachuk, D. V. et al., Farm Zh, 1978, (3), 71-73, (Abstract).
Rybachuk, D. V. et al., Farm Zh, 1978, (4), 87-89, (Abstract).
Sykulska, Z. et al., Farm Pol, 1966, 22, 510-4, (Abstract).
Hoevernaars, P. C., Pharm Weekly, 1965, 100, 1151-62, (Abstract).
Sykulska, A., Acta Pol Pharm, 1965, 22, 133-39, (Abstract).
Kurchenko, I. N., Farm Zh, 1976, 31 (2), 86-87, (Abstract).
Litovkina, E. G., Farm Zh, 1978, 12 (3), 123-7, (Abstract).
Parenteral Drug Association, Parenteral Dosage Forms, 1959-1963.
Remington's Pharmaceutical Sciences, Philadelphia College of Pharmacy and Science, 1980, 1480-1481.
*Modern Pharmaceutics,* G. S. Banker and C. T. Rhodes, pp. 429 and 456.

*Primary Examiner*—Jerome D. Goldberg
*Attorney, Agent, or Firm*—Bacon & Thomas

[57] ABSTRACT

A solid pharmaceutical composition comprising one or more β-lactam antibiotics in acid or amphoteric form in association with at least one physiologically acceptable base in the presence of a gaseous atmosphere containing a stabilizing amount of carbon dioxide at a concentration greater than that of atmospheric air. The compositions exhibit enhanced stability. A preferred antibiotic for the compositions is ceftazidime or a hydrate thereof, and a preferred base is sodium carbonate or a mixture thereof with one or more other bases.

20 Claims, No Drawings

PHARMACEUTICAL COMPOSITIONS

This invention concerns improvements in or relating to pharmaceutical compositions. In particular, the invention relates to pharmaceutical compositions containing β-lactam antibiotics.

β-Lactam antibiotics are often administered by injection as a solution in a sterile aqueous vehicle. The antibiotics are commonly amphoteric or acidic compounds which are relatively insoluble in water and are advantageously present in such solutions as water-soluble salts formed with bases, e.g. the sodium salts. It has been proposed to formulate β-lactam antibiotics with a solid base such as sodium carbonate so that on dissolution in a sterile aqueous injection medium, a water-soluble salt is formed by reaction between the antibiotic and the base. This may be done for example, where no stable water-soluble physiologically acceptable salt of the antibiotic has been found. However, it has been found that even such formulations can be unstable on large scale handling and subsequent storage even with exclusion of oxygen by using an atmosphere of nitrogen.

We have now surprisingly found that the stability of solid compositions containing a β-lactam antibiotic and a base can be significantly improved by formulating the compositions with an atmosphere containing carbon dioxide. A marked effect on stability can be observed even with gas mixtures, e.g. nitrogen, containing carbon dioxide at concentrations as low as 10% by volume or even less.

Thus, the invention provides a solid pharmaceutical composition comprising one or more β-lactam antibiotics in acidic or amphoteric form in association with at least one physiologically acceptable base in the presence of a gaseous atmosphere containing a stabilising amount of carbon dioxide at a concentration greater than that of atmospheric air.

β-Lactam antibiotics which may be incorporated into the compositions according to the invention include, for example, cephalosporin compounds such as cefamandole, cefazolin, cephalexin, cephaloglycin, cephalothin, cephapirin, cephradine, cefaclor, cefadroxil, cefoxitin, cefatrizine, cefazoflur, cefazedone, ceforanide, cefsulodin, ceftezole, cephacetrile, cephanone, cefuroxime, cephoxazole, cefroxadine, cefmetazole, cefonicid, cefoperazone, cefotiam, cefotaxime, cefmenoxime, ceftizoxime, ceftriaxone, cefodizime, cefotetan, lamoxactam, cephaloridine in the form of an acid addition salt, e.g. the hydronitrate, ceftazidime, (6R,7R)-3-acetoxymethyl-7-[(Z)-2-(fur-2-yl)-2-methoxyiminoacetamido]-ceph-3-em-4-carboxylic acid, (6R,7R)-7-[(Z)-2-(2-aminothiazol-4-yl)-2-cyclopropylmethoxyiminoacetamido]-3-(1-pyridiniummethyl)ceph-3-em-4-carboxylate, (6R,7R)-7-[(Z)-2-(2-aminothiazol-4-yl)-2-cyclopropylmethoxyiminoacetamido]-3-carbamoyloxymethylceph-3-em-4-carboxylic acid, and (6R,7R)-7-[(Z)-2-(1-carboxycyclobut-1-oxyimino)-2-(fur-2-yl)acetamido]-3-carbamoyloxymethylceph-3-em-4-carboxylic acid; penicillins such as penicillin G, penicillin V, amoxycillin, ampicillin, carbenicillin, cloxacillin, dicloxacillin, flucloxacillin, methicillin, nafcillin, oxacillin, phenethicillin and ticarcillin; clavulanic acid; thienamycins such as N-formimidoylthienamycin; monocyclic β-lactams such as azthreonam; and mixtures thereof. Antibiotics such as ceftazidime which contain basic groups may also be in the form of their acid addition salts, e.g the hydrochlorides. Compositions containing mixtures of antibiotics may for example contain two such antibiotics, such as a mixture of amoxycillin and clavulanic acid or of ampicillin and flucloxacillin.

The β-lactam compounds will normally be present in a form capable of reacting with a base, i.e. in an acidic or amphoteric form, which may optionally be solvated e.g. hydrated. It will be appreciated that where compositions according to the invention contain more than one β-lactam antibiotic it is possible that only one of the antibiotic compounds is in an acidic or amphoteric form.

β-Lactam antibiotics which may be particularly preferred for formulating into compositions according to the invention include, for example, ceftazidime, cephaloridine hydronitrate, cefoperazone, cefotaxime, cefsulodin, cefmenoxime and penicillin V.

Bases which may be used in the compositions according to the invention include, for example, alkali metal carbonates such as sodium or potassium carbonate; alkali metal bicarbonates such as sodium bicarbonate; alkali metal or ammonium phosphates such as sodium phosphate; ammonium carbonate; guanidine carbonate; organic bases such as phenylethylbenzylamine, dibenzylethylenediamine, ethanolamine, diethanolamine, N-methylglucosamine, N-methylglucamine, sodium glycinate, lysine, lysine acetate, tromethamine, guanidine and arginine; and mixtures thereof. In general, the base component preferably includes at least one base capable of reacting with carbon dioxide and water; thus, for example, a carbonate may react in this way to form a bicarbonate, or a strong organic base, such as arginine, may react to form a carbonate.

A preferred composition of the invention contains ceftazidime, which may advantageously be present in the form of a hydrate e.g. the crystalline pentahydrate described in British Patent Specification No. 2063871, together with sodium carbonate, advantageously in an anhydrous form.

The ratio of base to β-lactam antibiotic in the compositions of the invention is desirably in the range of (0.8 to 6.0) equivalents of base to one equivalent of antibiotic and preferably about 0.9 to 4.0:1. In some cases ratios of base to β-lactam as low as 0.5 may be useful. As indicated above, a mixture of bases may be used in which one component is generally capable of reacting with carbon dioxide and water. It may thus be convenient to use mixtures of sodium carbonate and bicarbonate. In mixtures of bases the component capable of reacting with carbon dioxide and water is preferably present in an amount of at least 0.05 equivalents per equivalent of antibiotic.

The amount of carbon dioxide in the compositions according to the invention may vary over wide limits. When the carbon dioxide is present in an atmosphere comprising a mixture of gases e.g. with air, the level of carbon dioxide will, of course, be substantially higher than the concentration of 0.03% by volume normally found in air. Thus, the atmosphere preferably contains at least 1%, more preferably at least 4% by volume of carbon dioxide. In general, however, we have found that the greatest stabilising effect is achieved with concentrations of carbon dioxide greater than about 10% by volume. In practice, it may be convenient to use higher concentrations of carbon dioxide, such as 50% or greater e.g. about 90% by volume.

The amount of carbon dioxide present is preferably sufficient to combine together with the base with any water present. The presence of water may arise by adsorption from the atmosphere, abrasion of crystalline hydrates or as residual solvent from the production process.

The compositions according to the invention are preferably provided in sealed containers e.g. ampoules or vials or bulk storage containers. Ampoules or vials are conveniently such as to provide a unit dose of the active ingredient e.g. for constitution with a sterile vehicle for injection, such as pyrogen-free water. The dosage units will generally contain conventional amounts of the antibiotic substance(s). For example, dosage units may conveniently contain 50 to 2000 mg of the active ingredient. The dosage of active ingredient employed for adult human treatment will preferably range from 500 to 6000 mg per day depending on the antibiotic used and the route and frequency of administration.

The invention also extends to mixtures of the components occurring during blending, handling and filling into sealed containers such as ampoules or vials.

The compositions according to the invention may be prepared by bringing at least one acidic or amphoteric β-lactam antibiotic in solid form, at least one physiologically acceptable base in solid form and an atmosphere containing a stabilising amount of carbon dioxide at a concentration greater than that of atmospheric air into association. For example, the β-lactam antibiotic and the base, both in particulate form, may be blended together in air to give a homogeneous particulate mixture which is then filled into appropriate containers which are subsequently purged with carbon dioxide or a gas mixture containing it. Alternatively, the solid components may be blended together in an atmosphere comprising carbon dioxide, and may if desired be subsequently filled into containers also in an atmosphere comprising carbon dioxide.

In a further method, one of the solid components is filled into the container, followed by filling with the other solid component without mixing (the so-called "double-filling" method), the two fillings optionally being effected in the presence of carbon dioxide. The containers may then, if necessary, be purged with carbon dioxide. It will be appreciated that the compositions prepared by this method will not comprise a homogeneous mixture of the solid components.

In a still further method, the containers may be filled with a solution of the base which is then dried, e.g. by freeze drying, before adding the active ingredient and purging with carbon dioxide. Alternatively, when the base to be used is sodium carbonate, the containers may be filled with sodium bicarbonate in dry form or in solution which is then heated to form solid sodium carbonate before adding the active ingredient and purging with the carbon dioxide.

When the compositions are in powder form, it will be appreciated that the carbon dioxide may be in the interstices between particles of the active ingredient and the base as well as in any headspace above the solid components.

The β-lactam antibiotic and base starting materials are preferably substantially free from water, other than water of crystallisation.

As indicated above, we have found that the stability of β-lactam antibiotic in the compositions of the invention may be surprisingly improved. For example, we have found that in storage tests at elevated temperatures, the rate of degradation of ceftazidime in compositions of the invention can be as little as a quarter of that of a blend in a vial with a nitrogen headspace.

The invention will now be illustrated in the following non-limiting Examples:

EXAMPLE 1

Formula per blend
Ceftazidime pentahydrate: 14.818 kg (on anhydrous basis)
Sodium carbonate (anhydrous): 1.725 kg The ceftazidime pentahydrate was blended aseptically with the sodium carbonate in a powder mixer. Quantities of this blend equivalent to 250 mg anhydrous ceftazidime were filled into glass vials. In each case the vial headspace was purged with carbon dioxide and the vial was closed using a rubber plug and a metal overseal applied by crimping. All operations were performed under sterile conditions.

The product may be constituted shortly before administration by dissolving the powder in water for injections.

EXAMPLE 2

Formula per blend
Ceftazidime pentahydrate: 15.200 kg (on anhydrous basis)
Sodium carbonate (anhydrous): 1.7695 kg The ceftazidime pentahydrate was blended aseptically with the sodium carbonate in a powder mixer with a blanket of sterile carbon dioxide. Quantities of this blend equivalent to 250 mg anhydrous ceftazidime were filled into glass vials. In each case the vial headspace was purged with carbon dioxide and the vial was closed using a rubber plug and a metal overseal applied by crimping.

The product may be constituted, shortly before administration by dissolving the powder in water for injections.

EXAMPLE 3

Formula per vial
Ceftazidime pentahydrate: 260 mg (on anhydrous basis)
Sodium carbonate (anhydrous): 30 mg The ceftazidime pentahydrate and sodium carbonate were accurately weighed into a glass vial and the headspace purged with carbon dioxide. A rubber plug was then inserted and a metal overseal applied by crimping.

The product may be constituted shortly before administration by dissolving the powder in water for injections.

EXAMPLE 4

General Method

The antibiotic was blended with the base using in each case the quantities given in Table 1. Quantities of the blend equivalent to 250 mg of the anhydrous antibiotic were filled into glass vials. In each case the vial headspace was purged with carbon dioxide. The vial was then closed using a rubber plug and a metal overseal applied by crimping.

TABLE 1

| Antibiotic | Weight (g) | Base | Weight (g) |
| --- | --- | --- | --- |
| Ceftazidime pentahydrate | 15 | Sodium carbonate | 1.500 |
| Cephaloridine hydronitrate | 10 | Sodium carbonate | 1.61 |

TABLE 1-continued

| Antibiotic | Weight (g) | Base | Weight (g) |
|---|---|---|---|
| Cefoperazone | 9 | Sodium carbonate | 0.89 |
| Cefotaxime | 7 | Sodium carbonate | 1.14 |
| Cefsulodin | 9 | Sodium carbonate | 1.08 |
| Cefmenoxime | 9 | Sodium carbonate | 1.49 |
| Ceftazidime pentahydrate | 10 | Guanidine carbonate | 1.70 |
| Cephalexin | 15 | Sodium carbonate | 4.13 |
| Ampicillin trihydrate | 10 | Sodium carbonate | 2.76 |
| Cefuroxime | 10 | Sodium carbonate | 1.75 |
| Cephalothin | 10 | Sodium carbonate | 1.60 |
| Compound A* | 10 | Sodium carbonate | 1.49 |
| Compound B+ | 10 | Sodium carbonate | 2.27 |
| Ceftazidime pentahydrate | 10 | Potassium carbonate | 2.08 |
| Ceftazidime pentahydrate | 15 | Arginine | 4.43 |
| Cephoxazole | 10 | Sodium carbonate | 1.27 |
| Ceftizoxime | 9 | Sodium carbonate | 1.74 |
| Pencillin V | 10 | Sodium carbonate | 2.27 |

*Compound A - (6R,7R)-3-acetoxymethyl-7-[(Z-2-(fur-2-yl)-2-methoxyiminoacetamido]ceph-3-em-4-carboxylic acid.
+Compound B - (6R,7R)-7-[(Z)-2-(1-carboxycyclobut-1-oxyimino)-2-(fur-2-yl)acetamido]-3-carbamoyloxymethylceph-3-em-4-carboxylic acid.

EXAMPLE 5

A powder blend of ceftazidime pentahydrate and anhydrous sodium carbonate in a weight ratio of 10:1 was weighed into glass vials using a target fill weight of 1.333 g. The headspace of each vial was purged with standard gas mixtures of carbon dioxide in nitrogen before being closed by using a rubber plug and a metal overseal applied by crimping. The gas mixtures consisted of 20, 10, 8, 6, 4 and 2% v/v carbon dioxide in nitrogen. Vials were also filled using 100% carbon dioxide.

EXAMPLE 6

Formula per blend
Ceftazidime pentahydrate: 1975 g
Arginine: 525 g
Sodium carbonate anhydrous: 19.73 g The ceftazidime pentahydrate was blended with the arginine and the sodium carbonate in a powder mixer. The blend was filled into glass vials, using a target fill weight of 773. mg per vial. Then the vial headspace was purged with carbon dioxide and the vial closed using a rubber plug and a metal overseal applied by crimping.

The product was dissolved, as for administration, by the addition of 1.5 ml Water for Injections.

EXAMPLE 7

Formula per vial
Ceftazidime pentahydrate: 1.212 g
Tromethamine: 0.2790 g
Sodium carbonate anhydrous: 0.0121 g The ceftazidime penhtaydrate, tromethamine and sodium carbonate were accurately weighed into a glass vial and the headspace purged with carbon dioxide. A rubber plug was then inserted and a metal overseal applied by crimping.

The product was dissolved, as for administration, by the addition of 3 ml Water for Injections.

EXAMPLE 8

Formula per vial
(6R,7R)—7[(Z)-2-(2-aminothiazol-4-yl)-2-cyclopropylmethoxyiminoacetamido]3-(1-pyridiniummethyl)ceph-3-em-4-carboxylate, bishydrochloride: 363 mg
Sodium carbonate anhydrous: 65.5 mg The cephalosporin antibiotic and the sodium carbonate anhydrous were accurately weighed into a glass vial and the headspace was purged with carbon dioxide. A rubber plug was then inserted and a metal overseal applied by crimping.

I claim:

1. A solid pharmaceutical composition comprising an effective amount of ceftazidime in association with at least one physiologically acceptable base in the presence of a gaseous atmosphere containing carbon dioxide in sufficient quantity to stabilize the ceftazidime and present at a concentration greater than the concentration of carbon dioxide in atmospheric air.

2. A composition according to claim 1 wherein the atmosphere contains at least 1% by volume of carbon dioxide.

3. A composition according to claim 2 wherein the atmosphere contains at least 4% by volume of carbon dioxide.

4. A composition according to claim 3 wherein the atmosphere contains at least 10% by volume of carbon dioxide.

5. A composition according to claim 3 which contains from 0.8 to 6.0 equivalents of base to one equivalent of ceftazidime.

6. A composition according to claim 5 which contains from 0.9 to 4 equivalents of base to one equivalent of ceftazidime.

7. A composition according to claim 1 wherein the base is arginine.

8. A composition according to claim 1 wherein the base is an alkali metal carbonate.

9. A composition according to claim 8 wherein the carbonate is sodium carbonate.

10. A composition according to claim 1 wherein ceftazidime is in a hydrated form.

11. A composition according to claim 10 wherein the hydrate is ceftazidime pentahydrate.

12. A composition according to claim 2 which contains from 0.8 to 6.0 equivalents of base to 1 equivalent of ceftazidime.

13. A composition according to claim 3 which contains from 0.9 to 4 equivalents of base to one equivalent of ceftazidime.

14. A composition according to claim 12 wherein the base is arginine.

15. A composition according to claim 12 wherein the base is an alkali metal carbonate.

16. A composition according to claim 13 wherein the base is sodium carbonate.

17. A composition according to claim 14 wherein the ceftazidime is a pentahydrate thereof.

18. A composition according to claim 15 wherein the ceftazidime is a hydrate thereof.

19. A composition according to claim 16 wherein the ceftazidime is a hydrate thereof.

20. A composition according to claim 19 wherein the hydrate is ceftazidime pentahydrate.

* * * * *